(12) United States Patent
Chen et al.

(10) Patent No.: US 12,006,353 B2
(45) Date of Patent: Jun. 11, 2024

(54) APPLICATION OF SCFV PROTEIN, CAR GENE EXPRESSION VECTOR, CAR-T CELL AND APPLICATION THEREOF

(71) Applicant: Long Chen, Kunming (CN)

(72) Inventors: Long Chen, Kunming (CN); Fake Yang, Kunming (CN); Fukun Chen, Kunming (CN); Huatao Niu, Kunming (CN); Yongzhu Pu, Kunming (CN); Jindan Li, Kunming (CN); Conghui Yang, Kunming (CN); Dongxue Chen, Kunming (CN)

(73) Assignee: Long Chen, Kunming (CN)

( * ) Notice: Subject to any disclaimer, the term of this patent is extended or adjusted under 35 U.S.C. 154(b) by 88 days.

(21) Appl. No.: 17/872,131

(22) Filed: Jul. 25, 2022

(65) Prior Publication Data

US 2023/0081753 A1    Mar. 16, 2023

(51) Int. Cl.
*C07K 16/00* (2006.01)
*C12N 5/0783* (2010.01)
*C12N 15/86* (2006.01)

(52) U.S. Cl.
CPC ............ *C07K 16/00* (2013.01); *C12N 5/0636* (2013.01); *C12N 15/86* (2013.01); *C07K 2317/622* (2013.01)

(58) Field of Classification Search
None
See application file for complete search history.

(56) References Cited

U.S. PATENT DOCUMENTS

| 2019/0201445 A1 | 7/2019 | Qi et al. |
| 2019/0322755 A1 | 10/2019 | Tamada et al. |
| 2020/0332255 A1 | 10/2020 | Lee et al. |

FOREIGN PATENT DOCUMENTS

| WO | WO-2010125162 A1 * | 11/2010 | ........... A61K 31/439 |
| WO | WO-2022092277 A1 * | 10/2021 | ............... C12N 5/10 |

OTHER PUBLICATIONS

Origene, TrueORF cDNA Clones, Lenti Particles, and PrecisionShuttle Vector System (Year: 2021).*
pLenti-EF1a-C-Myc-DDK-P2A-Puro Lentiviral Gene Expression Vector Product Guide (Cat. No. PS100120) (Year: 2021).*

* cited by examiner

*Primary Examiner* — Daniel E Kolker
*Assistant Examiner* — Maureen Varina Driscoll
(74) *Attorney, Agent, or Firm* — Zhigang Ma (57) ABSTRACT

An application of SCFV protein in preparation of a CAR gene expression vector is disclosed. The protein sequence of the SCFV protein is shown in SEQ ID No. 1. The 1st~21st amino acids are the extracellular signal peptide amino acid sequences. The 22nd~31st amino acids are Flag amino acid sequences. And the remaining sequences are CXCR4 scfv sequences. An application of the gene sequence encoding the SCFV protein in preparation of a CAR gene expression vector is disclosed, and the gene sequence is shown in SEQ ID No.2. A CAR gene expression vector and a CAR-T cell are disclosed. The expression vector is plent-EF1a-Flag-CXCR4 CAR, and CAR-T cells are used in the preparation of a drug for a targeted therapy of tumor cells with high expression of CXCR4.

6 Claims, 7 Drawing Sheets

Specification includes a Sequence Listing.

SEQUENCE LISTING

```
Sequence total quantity: 2
SEQ ID NO: 1              moltype = AA   length = 384
FEATURE                   Location/Qualifiers
source                    1..384
                          mol_type = protein
                          note = SCFV amino acid sequence of human CXCR4 gene
                          organism = synthetic construct
SEQUENCE: 1
MALPVTALLL PLALLLHAAR PDYKDDDDKG SEVQLVESGG GLVQPGRSLR LSCTASGFTF    60
TDNYMSWVRQ APGKGLEWVG FIRNKANGYT TEYAASVKGR FTISRDDSKS IAYLQMNSLK   120
TEDTAVYYCA RDVGSNYFDY WGQGTLVTVS SQLKSSGSGS ESKSTDIVMT QSPSSLAVSL   180
GERATMSCKS SQSLFNSRTR KNYLAWYQQK PGQSPKLLIY WASARDSGVP ARFTGSGSET   240
YFTLTISRVQ AEDLAVYYCM QSFNLRTFGQ GTKVEIKTRT VAAPSVFIFP PSDEQLKSGT   300
ASVVCLLNNF YPREAKVQWK VDNALQSGNS QESVTEQDSK DSTYSLSSTL TLSKADYEKH   360
KVYACEVTHQ GLSSPVTKSF NRGE                                         384

SEQ ID NO: 2              moltype = DNA   length = 1059
FEATURE                   Location/Qualifiers
source                    1..1059
                          mol_type = other DNA
                          note = the gene sequence encoding the SCFV protein
                          organism = synthetic construct
SEQUENCE: 2
gaggtgcagc tggtggagag cggcggcgga ctggtgcagc ctggaagatc tctgagactg    60
agctgcacag cctccggctt tactttcaca gataattata tgtcttgggt gagacaggca   120
ccaggcaaag gcctggagtg ggtgggcttt atcagaaata aggccaacgg atatactact   180
gaatatgccg cctctgtgaa gggaagattc actatctcta gagatgactc taaatccata   240
gcctacctcc agatgaatag cctgaaaact gaagatacag cagtgtacta ctgtgctagg   300
gatgtgggct ccaactactt cgactactgg ggccaaggca ccctggtgac cgtgagcagc   360
cagctgaagt ccagcggcag cggcagcgag agcaagagca ccgacatcgt gatgacccag   420
tctcctcca gcctggccgt gagcctgggc gagcgggcca caatgagctg caagtctagc   480
cagagcctgt tcaatagcag aaccaggaag aactacctgg cctggtacca gcagaagccc   540
ggccagagcc ccaagctgct gatctactgg gcctccgcca ggacagcggc cgtgcccgcc   600
aggttcaccg gcagcggcag cgagacctac tttaccctga ccatctccag agtgcaggcc   660
gaggacctgg ccgtgtacta ctgcatgcag agcttcaacc tgagaacctt cggccagggc   720
accaaggtgg agatcaagac caggaccgtg gccgccccca gcgtgtttat ctttcccccc   780
agcgacgagc agctgaagtc cggcaccgcc tccgtggtct gcctgctgaa caacttctac   840
cctagggagg ccaaggtgca gtggaaggtg gacaacgccc tgcagagcgg caatagccag   900
gagtccgtga ccgagcagga cagcaaggac agcacataca gcctgagctc caccctgacc   960
ctgagcaagg ccgactacga gaagcacaag gtgtacgcct gtgaggtgac ccaccagggc  1020
ctgagcagcc ccgtgaccaa gagcttcaat agaggcgag                         1059
```

APPLICATION OF SCFV PROTEIN, CAR GENE EXPRESSION VECTOR, CAR-T CELL AND APPLICATION THEREOF

REFERENCE TO SEQUENCE LISTING

The Substitute Sequence Listing XML file is submitted to replace the sequence listing XML file previously submitted via the USPTO Patent Center, with a file name of "Substitute_Sequence_Listing_SJDL-USP1222867-97-889", a creation date of Nov. 20, 2022, and a size of 4552 KB. The Substitute Sequence Listing XML file is a part of the specification and is incorporated in its entirety by reference herein.

TECHNICAL FIELD

The present disclosure relates to the technical field of molecular biology, and more specifically, to a recombinant protein, a CAR gene expression vector, a CAR-T cell and applications thereof.

BACKGROUND ART

Lung cancer is a common malignant tumor that seriously endangers human health. Studies have found that its receptor CXCR4 plays an important role in promoting the specific metastasis of tumor organs. CXCR4 is an important factor for tumor cells to penetrate the extracellular matrix, break away from the primary site, and invade into the surrounding tissues of tumors, and can promote the migration and homing of hematopoietic stem progenitor cells and hematopoietic progenitor cells. The expression of CXCR4 is lower in normal lung tissue, but higher in lung cancer. Chimeric antigen receptor modified T cells (CAR-T cells) therapy is a most rapidly developing adoptive cellular immunotherapy. In this technology, chimeric antigen receptors (CARs, also known as chimeric T cell receptors) are designed to be expressed on host T cells and induce a synthetic construct against the lung cancer CXCR4 antigen, thereby targeting the lung cancer cell surface antigen CXCR4, to mediate antitumor effects.

Studies have found that the expression of CXCR4 in lung cancer tissue had no correlation with the age and gender of the patients, but was correlated with the degree of differentiation, TNM stage, pathological type and lymph node metastasis. The early symptoms of lung cancer are not typical and there is a lack of effective detection methods. The cancer cells have already metastasized when many patients go to the doctor, so that the best operation time is missed. In addition, radiotherapy, chemotherapy and other treatment methods have certain limitations in patient selection. Therefore, it is very important to find new therapeutic targets for lung cancer Therefore, how to provide a chimeric antigen receptor recombinant protein and use it to prepare CAR gene expression vector and CAR-T cells is an urgent problem for those skilled in the art to solve.

SUMMARY

In view of above, the disclosure ligates the SCFV protein coding gene with the lentivirus vector, constructs the CAR gene expression vector, and then integrates the CAR gene into T cells, so that the SCFV protein coding gene can be transcribed and translated, and expressed on the surface of T cells to become a chimeric antigen receptor CAR, so as to achieve the effect of targeting against CXCR4 antigen.

In order to achieve the above purpose, technical schemes of the present disclosure are specifically described as follows.

An application of SCFV protein in preparation of a CAR gene expression vector is provided. The protein sequence of the SCFV protein is shown in SEQ ID No.1. The 1st~21st amino acids are the extracellular signal peptide amino acid sequences. The 22nd~31st amino acids are Flag amino acid sequences. And the remaining sequences are CXCR4 scfv sequences.

As the same inventive concept as the above technical scheme, the disclosure also requests to protect an application of the gene sequence encoding the SCFV protein in preparation of a CAR gene expression vector, and the gene sequence is shown in SEQ ID No.2.

As the same inventive concept as the above technical scheme, the disclosure also requests to protect a CAR gene expression vector, and the expression vector is plent-EF1a-Flag-CXCR4 CAR.

As the preferred technical scheme of the above technical scheme, plent-EF1a is a lentivirus vector obtained by enzyme digestion of plent-EF1a-EGFP vector with AsisI and MluI, and Flag-CXCR4 CAR is a recombinant plasmid obtained by enzyme digestion with AsisI and MluI on the basis of the sequence shown in SEQ ID No.2.

As the same inventive concept as the above technical scheme, the disclosure also requests to protect a method for constructing CAR gene expression vector. The method includes the following steps. Enzyme digestion is performed on the vector containing CXCR4 CAR and the lentivirus vector plenti-EF1a-EGFP separately to obtain a digested product. The digested product is ligated at 22° C. for 2 h to obtain a ligated product. Then the ligated product is purified and recovered the to obtain the CAR gene expression vector.

As the same inventive concept as the above technical scheme, the disclosure also requests to protect a recombinant cell for promoting CAR gene expression vector, which is formed by transforming the plent-EF1a-Flag-CXCR4 CAR recombinant plasmid, PMD2G plasmid and PSPAX2 plasmid into HEK293T cell.

As the same inventive concept as the above technical scheme, the disclosure also requests to protect a CAR-T cell. The CAR-T cells are formed by infecting T cells with the plent-EF1a-Flag-CXCR4 CAR.

As the same inventive concept as the above technical scheme, the disclosure also requests to protect an application of the recombinant protein in preparation of a drug for a targeted therapy of tumor cells with high expression of CXCR4.

As the same inventive concept as the above technical scheme, the disclosure also requests to protect an application of the CAR gene expression vector in preparation of a drug for a targeted therapy of tumor cells with high expression of CXCR4.

As the same inventive concept as the above technical scheme, the disclosure also requests to protect an application of the CAR-T cells in preparation of a drug for a targeted therapy of tumor cells with high expression of CXCR4.

According to the above technical scheme, compared with the prior art, the disclosure has the following beneficial effects. The SCFV protein of the present disclosure is applied to prepare the CAR gene expression vector, then infects T cells, transcribes and translates to obtain CAR protein, which can specifically combine with CACR4 antigen on the surface of tumor cells, and improve the targeted therapy effect of tumor cells.

BRIEF DESCRIPTION OF THE DRAWINGS

In order to explain the embodiments of the present disclosure or the technical solutions in the prior art more clearly, the following drawings that need to be used in the description of the embodiments or the prior art will be briefly introduced. Obviously, the drawings in the following description are only embodiments of the present disclosure. For those of ordinary skill in the art, other drawings can be obtained based on the drawings disclosed without creative work.

DETAILED DESCRIPTION OF THE EMBODIMENTS

Technical solutions of the present disclosure will be clearly and completely described below with reference to the embodiments. Obviously, the described embodiments are only part of the embodiments of the present disclosure, not all of them. Based on the embodiments of the disclosure, all other embodiments made by those skilled in the art without sparing any creative effort should fall within the protection scope of the disclosure.

Embodiment 1 Construction of plent-EF1a-Flag-CXCR4 CAR Plasmid

1. Sequence Synthesis

CXCR4 ScFv sequence was synthesized by the whole gene. CD8a signal peptide and Flag sequence were added at the N-terminal And it was cloned into lentivirus expression plasmid plent-EF1a-EGFP by using Asisi and MluI enzyme digestion sites. The plasmid was Amp resistant.

The SCFV sequence is as follows:
GAGGTGCAGCTGGTG-
GAGAGCGGCGGCGGACTGGTGCAGCCTGGAA-
GATCTCTG AGACTGAGCTGCACAGCCTCCGGCTT-
TACTTTCACAGATAATTATATGTCTTGGGTGAGAC
AGGCACCAGGCAAAGGCCTGGAGTGGGTGGGCTT-
TATCAGAAATAAGGCCAACGGATATA CTACT-
GAATATGCCGCCTCTGTGAAGGGAAGATTCAC-
TATCTCTAGAGATGACTCTAAATCC
ATAGCCTACCTCCAGATGAATAGCCTGAAAACT-
GAAGATACAGCAGTGTACTACTGTGCTA
GGGATGTGGGCTCCAACTACTTCGACTACTGGGGC-
CAAGGCACCCTGGTGACCGTGAGCA GCCAGCT-
GAAGTCCAGCGGCAGCGGCAGCGAGAGCAAG
AGCACCGACATCGTGATGACC
CAGTCTCCCTCCAGCCTGGCCGT-
GAGCCTGGGCGAGCGGGCCACAAT-
GAGCTGCAAGTCT AGCCAGAGCCTGTT-
CAATAGCAGAACCAGGAAGAACTACCTGGCCT
GGTACCAGCAGAA GCCCGGCCAGAGCCC-
CAAGCTGCTGATC-
TACTGGGCCTCCGCCAGGGACAGCGGCGTGC
CCGCCAGGTTCACCGGCAGCGGCAGCGAGACC-
TACTTTACCCTGACCATCTCCAGAGTGC
AGGCCGAGGACCTGGCCGTGTACTACTG-
CATGCAGAGCTTCAACCTGAGAACCTTCGGCC
AGGGCACCAAGGTGGAGATCAA-
GACCAGGACCGTGGCCGCCCCCAGCGTGTT-
TATCTTTC CCCCAGCGACGAGCAGCT-
GAAGTCCGGCACCGCCTCCGTGGTCTGCCTGCT
GAACAACT TCTACCCTAGGGAGGC-
CAAGGTGCAGTG-
GAAGGTGGACAACGCCCTGCAGAGCGGCAAT
AGCCAG-
GAGTCCGTGACCGAGCAGGACAGCAAGGACAGCA-
CATACAGCCTGAGCTCCAC CCTGACCCT-
GAGCAAGGCCGACTACGAGAAGCACAAGGTG
TACGCCTGTGAGGTGACCC ACCAGGGCCT-
GAGCAGCCCCGTGACCAAGAGCTT-
CAATAGAGGCGAG, as shown in SEQ ID No.2.

SCFV amino acid sequence of human CXCR4 gene is as follows:
Met Ala Leu Pro Val Thr Ala Leu Leu Leu Pro Leu Ala Leu Leu Leu His Ala Ala Arg Pro Asp Tyr Lys Asp Asp Asp Asp Lys Gly Ser Glu Val Gln Leu Val Glu Ser Gly Gly Gly Leu Val Gln Pro Gly ArgSer Leu Arg Leu Ser Cys Thr Ala Ser Gly Phe Thr Phe Thr Asp AsnTyr Met Ser Trp Val Arg Gln Ala Pro Gly Lys Gly Leu Glu Trp ValGly Phe Ile Arg Asn Lys Ala Asn Gly Tyr Thr Thr Glu Tyr Ala Ala Ser Val Lys Gly Arg Phe Thr Ile Ser Arg Asp Asp Ser Lys Ser Ile Ala Tyr Leu Gln Met Asn Ser Leu Lys Thr Glu Asp Thr Ala Val Tyr Tyr Cys Ala Arg Asp Val Gly Ser Asn Tyr Phe Asp Tyr Trp Gly Gln Gly Thr Leu Val Thr Val Ser Ser Gln Leu Lys Ser Ser Gly Ser Gly Ser Glu Ser Lys Ser Thr Asp Ile Val Met Thr Gln Ser Pro Ser Ser Leu Ala Val Ser Leu Gly Glu Arg Ala Thr Met Ser Cys Lys Ser Ser Gln Ser Leu Phe Asn Ser Arg Thr Arg Lys Asn Tyr Leu Ala Trp Tyr Gln Gln Lys Pro Gly Gln Ser Pro Lys Leu Leu Ile Tyr Trp Ala Ser Ala Arg Asp Ser Gly Val Pro Ala Arg Phe Thr Gly Ser Gly Ser Glu Thr Tyr Phe Thr Leu Thr Ile Ser Arg Val Gln Ala Glu Asp Leu Ala Val Tyr Tyr Cys Met Gln Ser Phe Asn Leu Arg Thr Phe Gly Gln Gly Thr Lys Val Glu Ile Lys Thr Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu, as shown in SEQ ID NO.1.

2. Enzyme Digestion and Ligation

The enzyme digestion is performed on the vector PUC57 containing CXCR4 CAR and lentivirus vector plent-EF1a-EGFP. The corresponding enzyme digestion system is shown in Table 1 and table 2:

TABLE 1

| Composition of reaction solution | Volume |
| --- | --- |
| DNA fragment (0.1 μg/μL) | 15 μL |
| 10× Buffer | 5 μL |
| AsisI | 1.5 μL |
| MluI | 1.5 μL |
| ddH$_2$O | 27 μL |
| Total | 50 μL |

TABLE 2

| Composition of reaction solution | Volume |
|---|---|
| Vector (0.5 µg/µL) | 2 µL |
| 10× Buffer | 5 µL |
| AsisI | 1.5 µL |
| MluI | 1.5 µL |
| ddH2O | 40 µL |
| Total | 50 µL |

Figure 1:
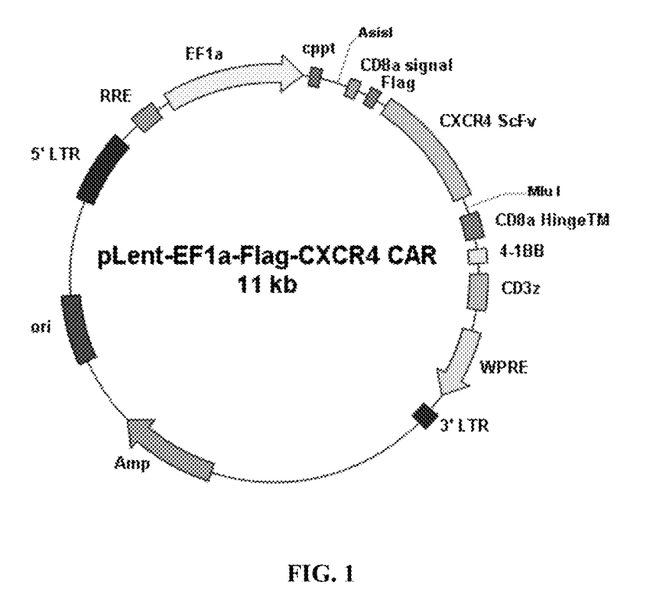
FIG. 1 is a map of the CAR gene expression vector plent-EF1a-Flag-CXCR4 CAR of the present disclosure.

The enzyme digestion was performed at 37° C. for 1 h after the sample was prepared and mixed well. After the reaction, the size of the enzyme digestion target band was detected by 1% agarose gel electrophoresis, and the target fragments were recovered by gel recovery kit. Micro centrifugation was preformed after mixing evenly, and the ligation was performed at 22° C. for 2 h to obtain the CAR gene expression vector plent-EF1a-Flag-CXCR4 CAR. The mass spectrum is shown in FIG. 1.

3. Transformation

The ligation product transformed the *Escherichia coli* DH5α competent cells and was spread into the corresponding resistant LB plate for screening.

The specific steps of the transformation are as follows.

(1) The prepared DH5a competent cells were taken out from −80° C. and put in an ice bath.

(2) After the DH5a competent cells were thawed, 1 µL of the ligation product was put into 20 µL of DH5a competent cells, fully mixed, and left in an ice bath for 30 minutes.

(3) The centrifuge tube was put into a 42° C. water bath for 40 seconds (do not shake the centrifuge tube during this period), and then quickly moved to an ice bath and stood for 2 minutes.

(4) 200 µL sterile LB medium (without antibiotics) was added into the centrifuge tube, mixed well, placed in a shaking table at 37° C., 200 rpm, and shaken for 1 hour. The purpose was to express the relevant resistance marker genes on the plasmid and resuscitate the bacteria.

(5) The above product was spread into the corresponding resistant solid medium plate.

Figure 2:
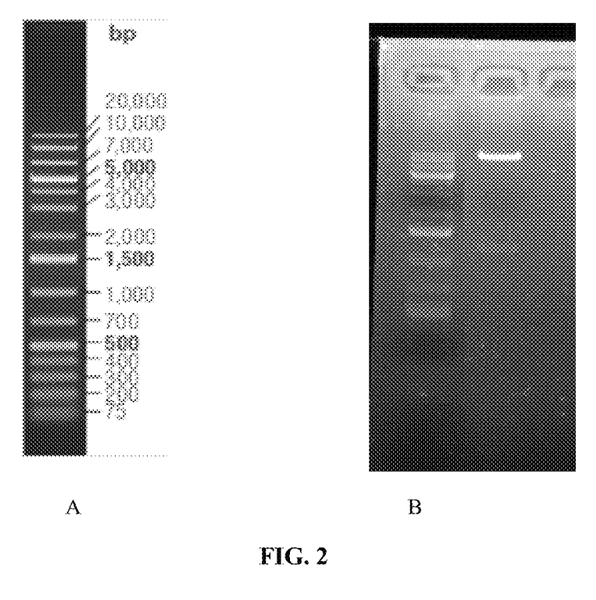
FIG. 2 is the gel electrophoresis diagram.

(6) Culture was performed overnight in a 37° C. incubator, a single colony was selected for culture, and the plasmid was extracted for enzyme digestion identification, and the positive clone gel is shown in FIG. 2.

Embodiment 2 CXCR4 CAR Lentivirus Packaging

The information of instruments and consumables is shown in Table 3 and Table 4.

TABLE 3

| Consumable | Article No. | Brand |
|---|---|---|
| Cell culture plate 10 cm | 704001 | NEST |
| Cell culture plate 15 cm | 715001 | NEST |
| 10 ml Serological pipette | 4488 | Corning |
| 50 ml Serological pipette | 4490 | Corning |
| 100-1250 Sterile extended cartridge gun head with scale | TF112-1000-Q | QSP |
| Cell cryopreservation tube | 377267 | Corning |
| DMEM High-sugar medium | C11965500BT | GIBICO |
| HEPES Solution 1M | SH30237.01 | HyClone |

TABLE 3-continued

| Consumable | Article No. | Brand |
|---|---|---|
| Penicillin Streptomycin Solution (100*) | C0222 | Beyotime |
| Fetal bovine serum | 1122050 | Gibico |
| 0.25% Trypsin | SH30042.01 | Hyclone |
| 10xPBS | ST476 | Beyotime |
| DMSO | D8372 | SOLARBIO |

TABLE 4

| Instrument | Specification and model | Brand |
|---|---|---|
| Biosafety cabinet | BSC-1300IIA2 | SUZHOU ANTAI AIRTECH CO., LTD (SAT) |
| Inverted microscope | CKX31SF | OLYMPUS |
| Carbon dioxide incubator | MCO-15AC | Sanyo Electric Co., Ltd |
| Quantitative polymerase chain reaction instrument (QPCR instrument) | CFX96 | BIO-RAD |
| Fluorescence microscope | ELWD0.3 | Nikon |
| Ultra-low temperature storage box | DW-86L386 | Qingdao Haier special instrument Co., Ltd |
| High speed refrigerated centrifuge | 1580R | LAB GENE Co., Ltd |

1. Virus Packaging Steps

Day1: 10 cmdish HEK293T cells with a degree of polymerization of 90% (about $6×10^7$ per plate) were transferred to 10 cmdish in the ratio of 1:3, and the cells reached a degree of polymerization of 90%-95% (about $6\%×10^7$ per plate) on the next day. The medium was DMEM high sugar medium of GIBICO (containing 10% FBS).

Day2:

No fluid changed before transfection.

The transfection reagent was configured according to the proportion in Table 5. below.

| | Mix 1 | Volume µL |
|---|---|---|
| 1 | DMEM (without FBS) | 1000 µL |
| 2 | Target gene plasmid | 10 µg |
| 3 | PMD2G | 3 µg |
| 4 | PSPAX2 | 6 µg |

Mix1 was mixed evenly and placed at room temperature for 5-10 min. 63 µl (1 µg/µl) PEI was added and mixed upside down evenly to obtain a mixture. Then the mixture was placed at room temperature for 5-10 min and added into 10 cm cell culture plate. (The cells reached a degree of polymerization of 90%, and too few cells would affect the transfection efficiency.)

Day3: the fluid was changed 6 hours after transfection.

Day5: the cell state was observed and taken photos after 72 h. The supernatant culture medium was collected, filtered with 0.45 µM membrane and removed the lysed HEK293T cells. The supernatant culture medium was added into the ultracentrifuge tube (355642) and centrifuged after balancing, at 25000 rpm, at 4° C. for 1.5 h. The supernatant was discarded, and 1 ml of virus preservation solution was used for redissolving, mixing and dissolving overnight.

Day6: the virus is collected for subpackaging, and the virus vector particle plent-EF1a-Flag-CXCR4 CAR was obtained.

2. Titer Detection

The titer was detected by the integration number method of lentivirus infected cells. The activity unit of lentivirus (integration number method) of WZ Bioscience Inc. was IU/mL, that is, the number of virus particles with biological activity contained in each milliliter of virus solution. For example, the virus titer≥1×10E$^9$ IU/mL means that there are at least 1×10$^9$ lentivirus particles with biological activity in each milliliter of virus solution.

Viral infection of cells included the following steps.
(1) HEK293 cells were uniformly inoculated at 2.5×105 cells/well in a 24-well cell culture plate 6 hours before infection.
(2) The lentivirus was diluted in gradients, and three gradients were made, that is, each well (500 μL DMEM medium without penicillin, streptomycin and serum) contained 10 μL, 10 μL and 0.1 μL virus. After shaking and mixing, it was added to the 24-well plate inoculated with cells. Before adding the virus, the medium in the plate was aspirated.
(3) After 18-20 hours of infection, the medium in the culture plate was replaced with fresh DMEM complete medium.
(4) After 64-68 hours of infection, cells were collected and genomic DNA was extracted.
(5) For each detection, a group of lentiviruses with known TU with fluorescence was set as a control to check the detected value.

3. Genomic DNA Extraction (Operating According to the Instructions of AxyGEN Genomic DNA Extraction Kit) and QPCR Detection
(1) With the gradient dilution of the detected lentivirus vector as the standard, QPCR was performed on the universal primers of the lentivirus vector to obtain the viral integrated copy number.
(2) With the gradient dilution of Actin plasmid as the standard, the genome copy number of the sample was detected by QPCR with Actin primers to obtain the genome copy number.
(3) SYBR Green Relatively Quantified the PCR Reaction System and Parameters The amplification system was shown in Table 6.

TABLE 6

| Template | 2 μL |
| --- | --- |
| 2× SYBR Green Mix | 10 μL |
| Upstream primer (10 μM) | 0.4 μL |
| Downstream primer (10 μM) | 0.4 μL |

Replenishing water to 20 μL

4. Calculation of Lentivirus IU (Integration Unit) ml$^{-1}$ $$IU/ml = (C \times N \times D \times 1000)/V$$

C=average number of lentiviral integrated copies per genome
N=number of cells at infection (approximately 2.5×10$^5$)
D=dilution multiple of virus
V=the volume of diluted virus added
The titer detection results are shown in Table 7.

| | Virus | Titer |
| --- | --- | --- |
| Results | Human CXCR4 gene CAR lentivirus | 2.0 × 10E9 IU/mL |
| | pLent-EF1a-EGFP Control lentivirus | 6 × 10E8 TU/mL |

Embodiment 3 T Cell Identification CD3 Positive Rate Test

Figure 3:
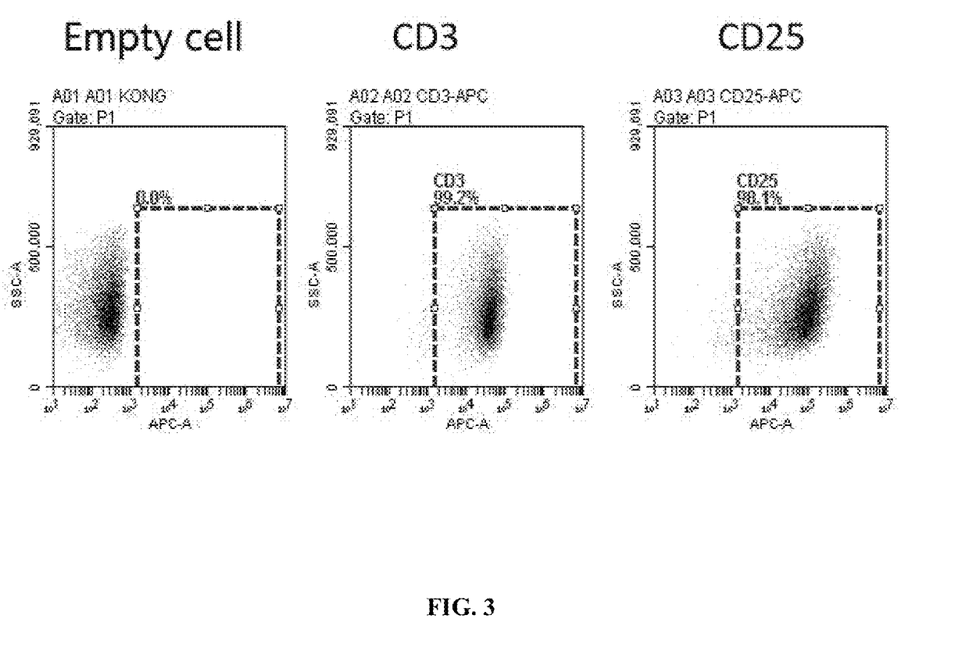
FIG. 3 is the diagram of the flow cytometry result.

1. Resuscitation of PBMC Cells
The culture medium was X-VIVO 15, CD3, CD28 antibody and IL-2 were added, and the culture density was controlled at 1-2*10^6/mL.
2. Test of CD3 Positive Rate of T Cells
The cells were cultured to D5 for flow cytometry, and CD3 and CD25 antibodies were stained.
3. Flow Test Results
The flow cytometry results are shown in FIG. 3, showing that the proportion of CD3$^+$ was 99.2% and the proportion of CD25+ (T cell activation marker) was 98.1%, indicating that T cell activation and expansion were successful.

Embodiment 4 CAR-T Cell Preparation and CXCR4 CAR Positive Rate Test

Figure 4:
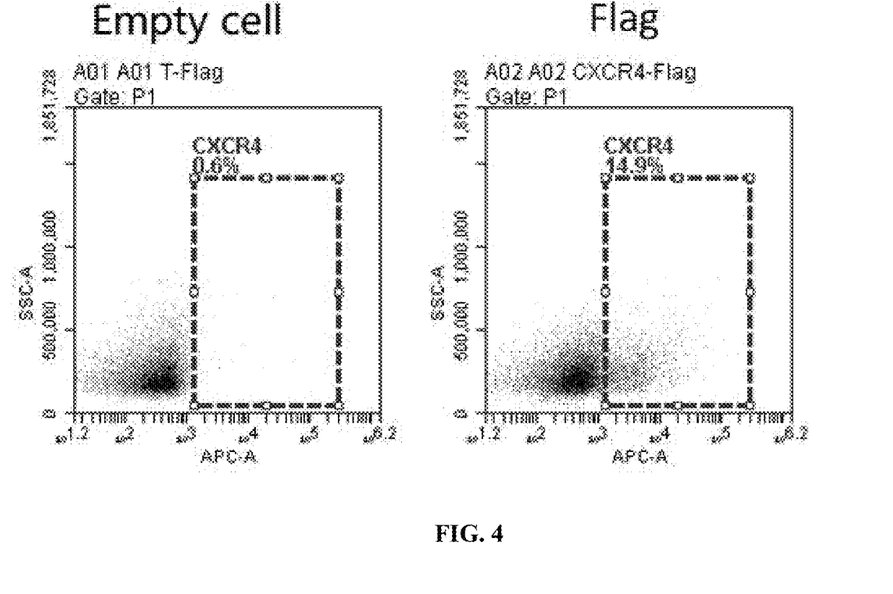
FIG. 4 is the diagram of the flow cytometry result.

1. Resuscitation of T Cells
The culture medium was X-VIVO 15, and the culture density was controlled at 1-2*10^6/ml.
2. Infection of T cells with lentivirus particle plent-EF1a-Flag-CXCR4 CAR
5*10^5 cells, 500 μL culture medium, virus according to MOI 20 and 5 μL LVTE (lentiviral transduction enhancer) were added into each well of the 24-well plate, mixed gently, centrifuged at room temperature for 45 min at 800×g, and placed into the incubator for 5-6 h after centrifugation. And then 500 μL culture medium was added. 48 h after infection, 1.2*10^6 cells were counted. The positive rate of CAR was identified by flow cytometry and flag antibodies were stained.
3. Flow Cytometry Results
The flow cytometry results are shown in FIG. 4, which shows that the proportion of positive CAR-T cells infected with CXCR4 was 14.9%.

Embodiment 5 Identification of CXCR4 Expression in Lung Cancer Cells

Figure 5:
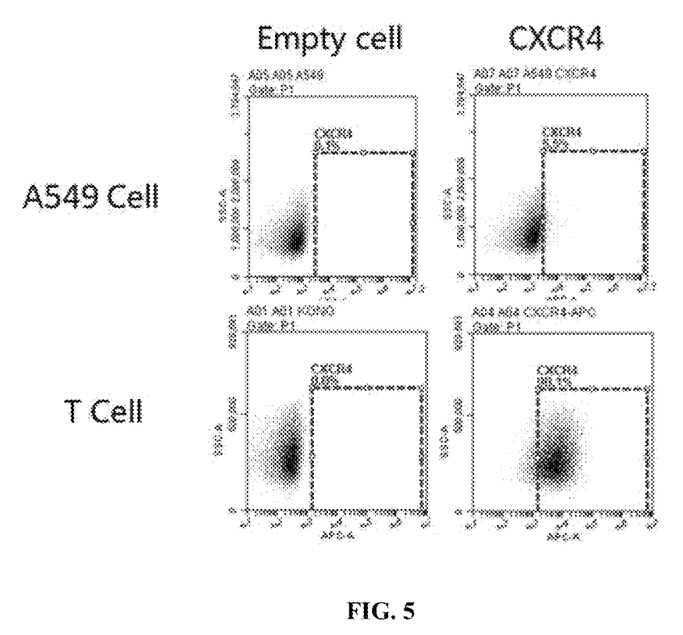
FIG. 5 is the diagram of the flow cytometry result.
Figure 6:
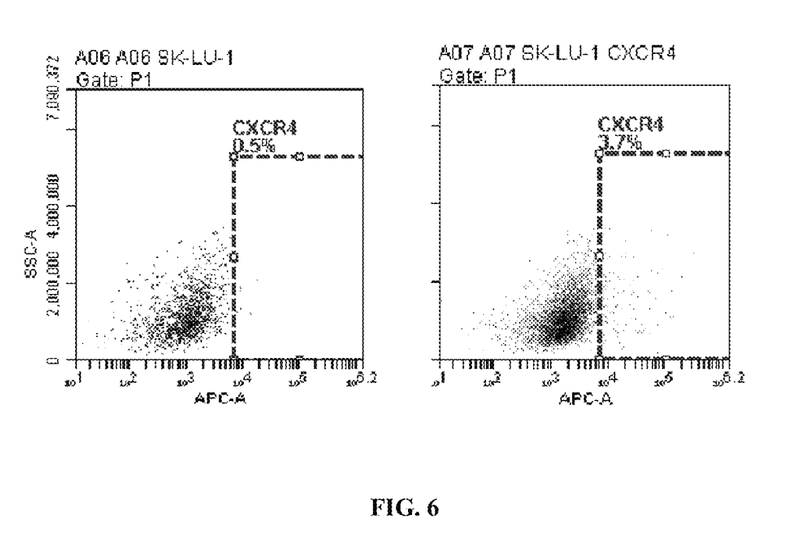
FIG. 6 is the diagram of the flow cytometry result.
Figure 7:
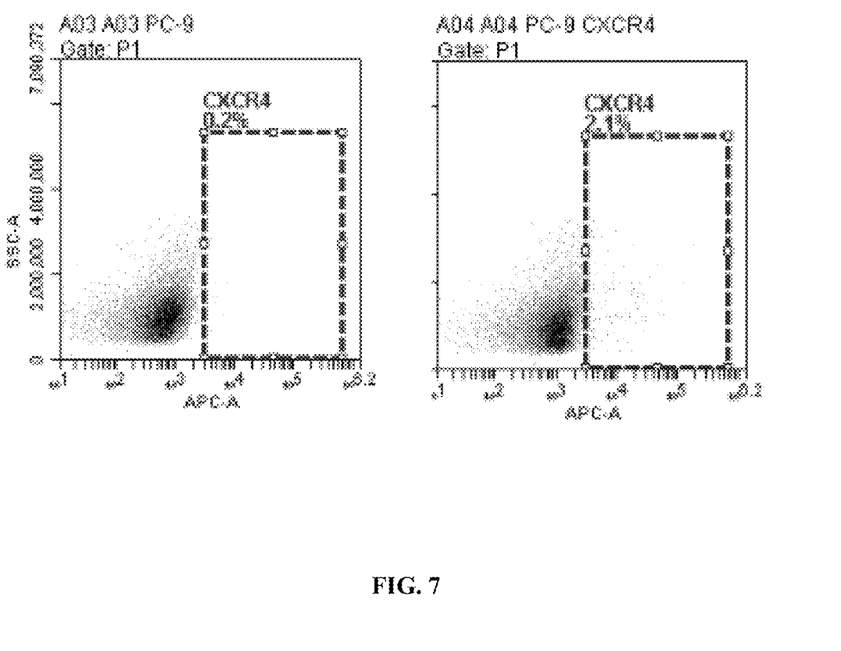
FIG. 7 is the diagram of the flow cytometry result.

1. Human lung cancer cell A549 and two poorly differentiated and highly metastatic human lung adenocarcinoma cell lines, SK-LU-1 and PC-9, were selected to identify the CXCR4 expression in these three cells by flow cytometry.
2. A549 cells were resuscitated in the medium of DMEM+ 10% FBS. After 2-5 days of culture, flow cytometry was performed and CXCR4 antibody was stained. The positive rate of CXCR4 in A549 cells was 5.5%, as shown in FIG. 5.
Note: at the same time, T cells were stained with CXCR4 antibody. It was found that T cells themselves also expressed CXCR4, and the positive rate reached 90%
3. SK-LU-1 cells were resuscitated in the medium of MEM+10% FBS. After 2-5 days of culture, flow cytometry was performed and CXCR4 antibody was stained. The positive rate of CXCR4 in SK-LU-1 cells was 3.7%, and the flow cytometry diagram is shown in FIG. 6.
PC-9 cells were resuscitated in the medium of DMEM+ 10% FBS. After 2-5 days of culture, flow cytometry was performed and CXCR4 antibody was stained. The positive rate of CXCR4 in PC-9 cells was 2.1%, and the flow cytometry diagram is shown in FIG. 7.

Various embodiments in the present specification are described in a progressive manner, and the emphasizing description of each embodiment is different from the other embodiments. The same and similar parts of various embodiments can be referred to for each other.

The above description of the disclosed embodiments enables those skilled in the art to realize or use the present disclosure. Many modifications to these embodiments will be apparent to those skilled in the art. The general principle defined herein can be realized in other embodiments without departing from the spirit or scope of the present disclosure. Therefore, the present disclosure will not be limited to these embodiments shown herein, but will conform to the widest scope consistent with the principle and novel features disclosed herein.

3. A CAR-T cell made by infecting T cells with the gene expression vector according to claim 2.

4. A method of constructing the CAR gene expression vector according to claim 2, comprising:
separately performing enzymatic digestion on a vector comprising the nucleic acid sequence set forth in SEQ ID NO: 2 and the lentiviral vector to obtain digested products;
ligating the digested products at 22° C. for 2 hours to produce a ligated product; and

What is claimed is:

1. A method of preparing a chimeric antigen receptor (CAR) gene expression vector, comprising ligating a nucleic acid that encodes a protein comprising the ScFv having the amino acid sequence set forth in SEQ ID NO: 1 into a vector, wherein amino acids 1-21 are extracellular signal peptide amino acid sequences; amino acids 22-31 are Flag amino acid sequences; and the remaining amino acid sequences are CXCR4 ScFv sequences.

2. A chimeric antigen receptor (CAR) gene expression vector, which is a lentivirus vector comprising the nucleic acid sequence set forth in SEQ ID NO: 2.

purifying and recovering the ligated product to obtain the CAR gene expression vector.

5. The method of constructing the CAR gene expression vector according to claim 4, wherein the nucleic acid sequence set forth in SEQ ID NO: 2 is obtained by digesting with the enzymes AsisI and MIuI.

6. The method of constructing the CAR gene expression vector according to claim 5, wherein the lentivirus vector is obtained by digesting with the enzymes AsisI and MIuI.

* * * * *